United States Patent
Shields

(10) Patent No.: US 6,478,780 B1
(45) Date of Patent: Nov. 12, 2002

(54) SHARPS SHIELD FOR DENTAL AND MEDICAL NEEDS

(76) Inventor: Jack W. Shields, 1950 Las Tunas Rd., Santa Barbara, CA (US) 93103

( * ) Notice: Subject to any disclaimer, the term of this patent is extended or adjusted under 35 U.S.C. 154(b) by 0 days.

(21) Appl. No.: 09/465,406

(22) Filed: Dec. 16, 1999

(51) Int. Cl.[7] ................................................ A61M 5/00
(52) U.S. Cl. ........................ 604/263; 604/192; 206/364
(58) Field of Search ............................... 604/162, 163, 604/164.07, 164.08, 171, 192, 194–199, 263; 206/364, 365; 128/919

(56) References Cited

U.S. PATENT DOCUMENTS

| | | | | |
|---|---|---|---|---|
| 3,008,570 A | * | 11/1961 | Roehr et al. | 206/229 |
| 4,892,525 A | * | 1/1990 | Hermann, Jr. et al. | 604/263 |
| 5,279,566 A | * | 1/1994 | Kline, Jr. et al. | 604/110 |
| 5,389,083 A | * | 2/1995 | McCarthy | 604/192 |
| 5,401,250 A | * | 3/1995 | Shields | 604/192 |
| 5,405,326 A | * | 4/1995 | Haber et al. | 604/110 |
| 5,558,648 A | * | 9/1996 | Shields | 604/192 |
| 5,558,649 A | * | 9/1996 | Shields | 604/192 |
| 5,713,873 A | * | 2/1998 | Jehle | 604/198 |
| 5,928,205 A | * | 7/1999 | Marshall | 604/263 |
| 5,997,513 A | * | 12/1999 | Smith et al. | 604/198 |
| 6,193,696 B1 | * | 2/2001 | Jansen et al. | 604/198 |
| 6,206,855 B1 | * | 3/2001 | Kunkel et al. | 604/192 |

* cited by examiner

Primary Examiner—Anhtuan T. Nguyen
Assistant Examiner—Cris Rodriguez

(57) ABSTRACT

I disclose a sharps shield for needles commonly used by dentists and plastic surgeons. The sharps shield has comprises a puncture-resistant graduated hollow cone having an open apex which reversibly wedge impacts and is hermetically sealed by the trailing end of a conical needle scabbard reversibly holding a hub-contained hollow bore steel needle sharp on each end; a mid-portion which reversibly wedge impacts the leading end of an inserted standard carpule aspirating syringe such that the trailing end of the needle can be reversibly affixed to drain a medication-containing carpule, when the conical needle scabbard is reversibly displaced; and an open trailing frustum which flares to substantially increase the internal diameter and reversibly hold a hermetically sealing cap. A similar graduated hollow cone is disclosed for shielding a Luer-Lok syringe-attachable standard hub-contained hollow-bore steel needle sharp on the leading end. Each sharps shield enables the user to conveniently affix the needle to the syringe under sterile conditions inside the mid-portion of the graduated hollow cone; to safely shield the syringe-attached needle inside the mid-portion of the graduated hollow cone before and between uses on a patient; and to safely dispose of the sharp needle after hub reinsertion into the needle scabbard reversibly wedge impacted in the open apex of the graduated hollow cone.

1 Claim, 2 Drawing Sheets

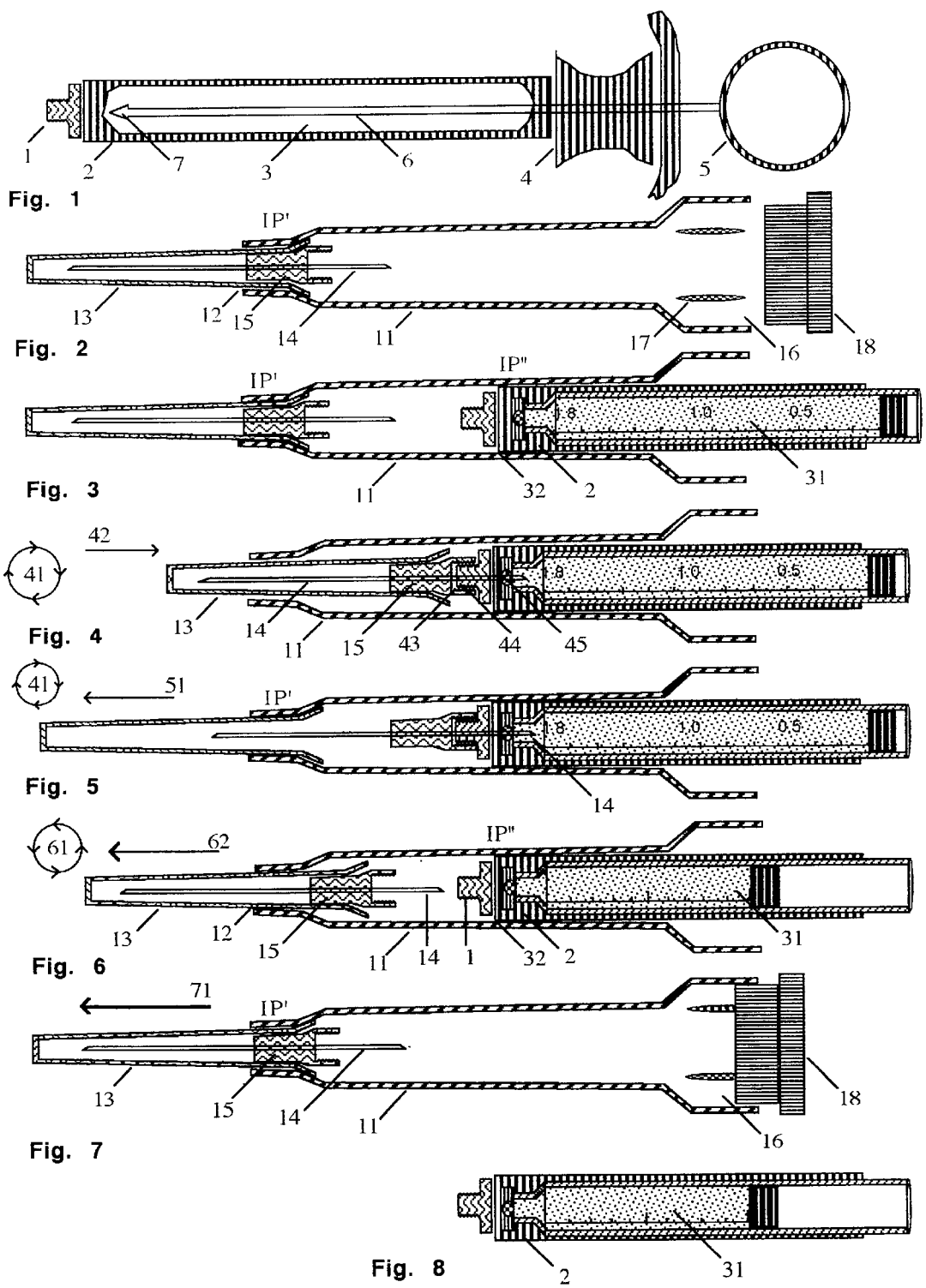

SHARPS SHIELD FOR DENTAL AND MEDICAL NEEDS

FIELD OF THE INVENTION

This invention relates to the sterile protection of hollow bore steel needles before, between and after uses with dental and medical syringes, and the prevention of accidental needlesticks in healthcare workers during use.

DESCRIPTION OF PRIOR ART

The evolution of bacterial resistance to many kinds of skin-borne and bloodborne infections, coupled with the ever-increasing use of hollow bore steel needles in patient care, mandate improved shielding of sharp needles before and after use under the mucous membranes or skin.

Currently, dentists customarily use carpule aspirating syringes to which an initially scabbard-shielded hollow bore steel needle, sharp on each end, is attached through a fitting on the leading end of sterilized, stainless steel, reusable syringe, after manual removal of a trailing needle scabbard. Then, a medication-filled cartridge, called a carpule, is inserted into the syringe, such that the trailing end of the sharp needle penetrates a diaphragm in the leading end of the carpule. After manual removal of the leading needle scabbard covering the sharp end of the needle used for injecting medications into patients, the armed carpule aspirating syringe is used once or more for giving anesthetic injections under oral mucous membranes or deeper injections into regional nerves. The leading end of the same needle, then, remains exposed for varying periods of time, depending on the kind of dental procedure performed and number of carpules inserted during the procedure. Because it is too hazardous for dental healthcare workers to "recap" the leading end of needle with the originally supplied sterile scabbard, the leading needle remains bare, unless other means are provided to protect the needle from bacterial contamination and/or causing accidental needlesticks between uses. After final use, the dentist is obliged to manually remove the needle safely, or to use some kind of device provided for disposing of the needle directly into a stationary sharps container, before cleansing and sterilizing the carpule aspirating syringe for use on another patient.

Currently, hollow bore steel needles sharp on the leading end covered by a single needle scabbard and disposable medical syringes are customarily supplied in separate sterile packages or attached together in a single sterile package. When the needle scabbard is removed in order to fill the sterile syringe from a sterile medication container, the exposed needle remains bare during transport to the patient and remains bare until after use for giving an intended subcutaneous, intramuscular or intravenous injection, unless some kind of protective device other than the original needle scabbard is provided. Needle protective devices currently in use include: sleeves on syringes which slide over the needles after use, spring mechanisms which retract needles into syringes after needle use, obturaters which extend blunt tips beyond nevel bevels with activation, and needle-hub-attached spring-loaded or hinging mechanisms which lock in place after the needle is withdrawn from a patient. A problem with many of these is that the needle remains exposed from the time of attached syringe filling with medication until withdrawal from a patient.

The use of puncture-resistant hollow cones with closed apices for inserting needles attached to syringes and other kinds of sharps, such a scalpel blades, was disclosed by Shields in U.S. Pat. No. 5,558,649 (Sep. 24, 1996). The instant patent application differs from U.S. Pat. No. 5,558,649 in that the apex of the hollow cone is left open and coned to reversibly wedge impact the scabbard of a standard dental anesthetic needle or a standard medical injection needle, along with the needle held in a hub which slip fits into the trailing open end of the needle scabbard. In effect, this eliminates the use of a scabbard fitting the trailing end of a dental anesthetic needle or a sterile package for dispensation of a medical needle not attached to a syringe. The original needle scabbard, then, becomes the needle shield.

A computer-based patent search for a similar graduated hollow cone with an open leading end and means for sterile closure of both ends, as well as reversibly connecting the hollow needle to the bore of a standard dental carpule or the bore of a standard medical syringe; and doing so inside the sterile mid-portion of the graduated hollow cone, proved negative. Monoject™ provides dental and medical syringes pre-attached to needles enclosed in hollow cones which look similar externally. However, internal wedge-impaction of the syringe into the conical holder for the syringe and needle, and use of the needle scabbard to reversibly attach the needle to the syringe inside of the conical holder are not claimed

SUMMARY

The objects of this invention are to provide simple cost-effective means for preventing cross-infections between patients and healthcare workers during the customary use of standard dental and medical hollow bore steel needles attached to syringes, as described in the Abstract. The magnitude of the problem is exemplified by the following statistics.

5–6 billion hollow bore steel needles are used annually during patient care in the USA. 600 million of these are needles sharp on each end used for giving dental anesthesia.

Annually 1–2 million Americans suffer from serious hospital acquired infections, most of which stem from needle injections. Blood stream infections, 25% fatal and costing an average of $33,000 per infection, account for 400,000 of such infections annually.

Annually some of eight million American healthcare workers suffer an estimated 600,000 to 800,000 accidental needlesticks, 0.3% resulting in HIV/AIDS infection since 1981. The rate of transmission of hepatitis B virus infection from an infected patient to a healthcare worker via a single accidental needlestick is estimated to be 6% to 30%. The rate of transmission of hepatitis C virus infection from an infected patient to a healthcare worker is currently estimated to 1.8% per accidental needle stick. Although vaccines have been developed to prevent HBV infections, there is no cure for HIV, HBV or HCV infections.

In health care facilities, patients are intentionally stuck with needles for injecting medications or withdrawing blood at the rate of 4–5 billion times annually.

The thrust of recent healthcare legislation has been toward protecting healthcare workers from accidental needlesticks. Never-the-less, patients and taxpayers pay for the needles.

BRIEF DESCRIPTION OF THE DRAWINGS (Scale is 1:1 in all drawings which are diagrammatic coronal sections in the central axis)

FIG. 1 shows the essential parts of a dental carpule aspirating syringe (CAS).

FIG. 2 shows the essentials of the conical invention, as applicable to the CAS.

FIG. 3 shows a carpule-loaded CAS inserted into to the point of wedge impaction into a graduated hollow cone (GHC), which is the central essence of the invention.

FIG. 4 shows conical needle scabbard containing a hubbed needle mated with the CAS'

FIG. 5 shows the needle transferred from the needle scabbard to the CAS.

FIG. 6 shows the needle transferred from the CAS back into the conical needle scabbard.

FIG. 7 shows the needle-containing scabbard safely wedge-impacted in the GHC.

FIG. 8 shows a partially spent carpule, after removal from the CAS.

DESCRIPTION OF PREFERRED EMBODIMENTS

Figure 9:
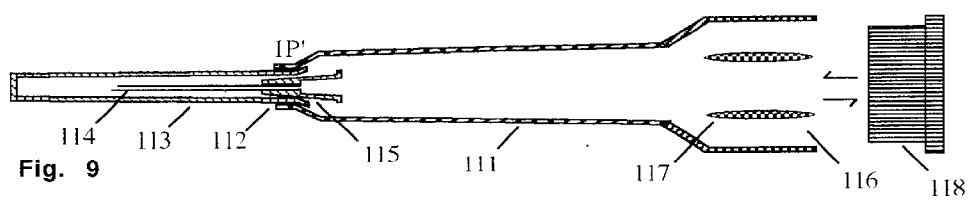
FIG. 9 shows the essentials of the GHC as applicable to a Luer-Lok syringe (LLS).

A. For Use With a Carpule Aspirating Syringe (CAS)

FIG. 1 (Prior Art) diagramatically shows the essential elements of a carpule aspirating syringe (CAS) commonly used by dentists and plastic surgeons to make sure that the leading end of a sharp hollow bore steel needle has not entered a blood vessel before giving local anesthesia with the dominant hand, while the index finger of the other hand feels for superficial and deep structures. If visible blood is aspirated back into the carpule inside the syringe, the user surmises that the needle bevel has been inserted into a vein, and that a local injection of selected soluble medications can be injected without resulting in an anaphylactic reaction in the patient. The essential elements pertinent to this description are: 1, a leading piece screwed into the body 2, such that a hollow needle can be attached and pass through into to a standard dental carpule in a hollow chamber 3 made to accommodate a standard 1.8 mL. carpule shown in FIGS. 3–7. The trailing parts of the CAS, including means for control 4 by the second and third fingers of the dominant hand 4 and a thumb ring 5 which activates the syringe plunger 6 whose leading end is fitted with a harpoon 7 for controlling forward and backward displacement of the piston inside a dental carpule. These mechanics are not depicted here, along with a spring mechanism holding an inserted dental carpule forward in the syringe bore. Concentrating on the leading end of the CAS, as it relates to the invention, items 4–7 will not be shown in the subsequent Figures, with the understanding that persons familiar with the art or dentistry will need no further explanation.

FIG. 2 shows the instant invention comprising a graduated hollow cone 11 having an open apex 12 which reversibly impacts IP' the trailing end of a conical tubular needle scabbard 13 holding a dental anesthetic needle 14 sharp on each end within a hub 15 which slip-connects into the trailing. open end of the needle scabbard 13. At the point of wedge impaction IP', the fit between the open apex 12 of the graduated hollow cone 11 and the trailing end of the conical needle scabbard 13 should hermetically seal the open apex 12 of the graduated hollow cone 11.

In the mid-portion of the graduated hollow cone 11, it should be noted that the slope of the puncture-resistant walls are uniform and long, in order to provide maximal surface contact with a cylindrical object inserted to a point of wedge impaction. In the open frustum 16 of the graduated hollow cone, the walls are flared sharply and, then, extended in cylindrical form for four reasons: (a) to maximize the diameter of a target area for insertion of a sharp needle attached to a cylindrical syringe; (b) to provide convenient protrusions for finger placement for users manipulating the graduated hollow cone with one hand; (c) to provide a properly oriented external surface for added longitudinal flutes 17 which will prevent rolling when the graduated hollow cone 11 is placed on a flat or sloped surface; and (d) to provide a cylindrical surface suitable for reversible insertion of a trailing cap 18 for hermetically sealing the graduated hollow cone 11 before use, as well as optional closure after use.

FIG. 3 shows the graduated hollow cone 11 with the leading end of a CAS 2 containing a standard 1.8 mL dental carpule 31 inserted to the point of wedge impaction IP" of the leading end the cylindrical syringe barrel 32.

FIG. 4. shows the graduated hollow cone 11 with the conical needle scabbard 13 disengaged from its point of wedge impaction IP' by manual clockwise rotation 41 and pushing 42 into the mid-portion of the cone until recessed threads 43 in the leading end of the needle hub 15 mate with corresponding protruding threads 44 on the leading piece 1 screwed into the body of the CAS 2, such that the trailing end of the needle 14 passes through the leading piece 1 and on through a penetrable diaphragm 45 in the leading end of the dental carpule 31 contained by the body of the CAS 3.

FIG. 5 shows the graduated hollow cone 11 after the conical needle scabbard 13 has been slip-disconnected from the needle hub 15 by clockwise rotation 41 and retraction 52 until again wedge impacted IP' in the open apex 12 of the graduated hollow cone. The needle-armed CAS, with the trailing end of the needle 14 now penetrating to drain the contents of the dental carpule 31, is ready for sterile use in a patient.

Actual use entails twisting and retracting the armed CAS from its point of wedge impaction IP" in the mid-portion of the graduated hollow cone 11 just before giving an injection into the patient Because dentists are prone to give multiple superficial mucosal or deep nerve injections in different parts of the mouth, depending on the kind of procedure, the CAS may be used more than once in a given procedure. Therefore, after each use and after the final use, the needle-armed CAS should be reinserted into the sterile confines of the graduated hollow cone to the point of wedge impaction. The tightness of the impaction between uses and after final use can be varied by the force used to insert and twist during CAS reinsertion. Although the needle will not be sterile after the first use, putting the armed CAS back into the graduated hollow cone between uses will preclude contamination of the needle with microorganisms foreign to the mouth of the patient and minimize the chances for accidental needle sticks in dental health care workers.

FIG. 6. shows a wedge impacted IP" leading end 32 of the CAS 2 containing a partially discharged carpule 31 after final use in a patient After advancement of the conical needle scabbard 13 from its point of wedge impaction IP' in the open apex 12 of the graduated hollow cone 11 to establish a firm slip connection to the needle hub 15, the needle hub 15 is disengaged from the leading piece 1 of the CAS 2 by means of counter-clockwise rotation 61, followed by retraction 62 of the needle scabbard 13. Then, the needle sharp on each end 14 no longer touches any part of the CAS 2, and is safely contained inside the graduated hollow cone 11.

FIG. 7 shows the graduated hollow cone 11, from whose cavity the CAS and contained dental carpule is withdrawn and a firm wedge impaction IP' has been re-established by forceful retraction 71 with counter- or clock-wise manual twisting of the conical needle scabbard 13. The needle hub 15 firmly slip-connected into the conical needle scabbard 13 will hold the needle sharp on each end 14 in a safe position until the graduated hollow cone 11 is disposed into a convenient sharps container sooner or later. As a fail-safe precaution, the trailing cap 18 can be re-inserted firmly into the open frustum 16 of the graduated hollow cone 11.

FIG. 8. shows the withdrawn leading end of the CAS 2 still containing the partly spent dental carpule 31. After removal form the CAS, the spent carpule should be disposed into a an appropriate waste container, such that the stainless steel CAS, as shown in FIG. 1 can be properly cleansed and sterilized for use again and again, more or less indefinitely.

Additional Specifications:
(1) The axial length of the conical needle scabbad 13 should exceed the axial length of the leading exposed shank of the longest needle sharp on each end 14 customarily used for giving dental anesthesia; and be long enough to leave the leading end of the conical needle scabbard 13 exposed for finger grasping when the trailing end of the scabbard is displaced sufficiently into the mid-portton of the graduated hollow cone 11 to enable reversible mating of the internal threads 43 on the conical needle hub 15 with the external 44 threads on the leading piece 1 of the CAS 2, when the leading end 32 of the CAS 2 is wedge impacted at IP" (as shown in FIG. 4). In addition, when the needle-armed CAS 2 is wedge impacted at IP", the needle bevel should not be able to touch the trailing end of a conical needle scabbard 13 wedge impacted at IP'. If obviously bent, the leading end of the needle should be inserted partway into the open frustum 16 of the graduated hollow cone 11 such that the needle bevel is protected and such that the shaft can be realigned by pressing against the side walls.
(2) The axial length of the graduated hollow cone 11 between the point of wedge impaction IP" of the CAS 2 and the trailing end of the open frustum 16 of theshould be sufficient to stabilize the inserted CAS 2 such that all components of the assembly align properly in the central axis.
(3) The addition of longitudinal external flanges 17 on the flared open frustum 16 of the graduated hollow cone 11 to prevent rolling is not an essential feature of the invention, but makes easier to perform a one-handed resheathing of a needle-armed CAS 2, if the graduated hollow cone 2 is left on a flat or slightly inclined surface during actual use of the CAS 2 in a patient. The large internal diameter of the open frustum 16 makes it possible to one-handedly insert the leading part of the needle 14 and the leading end of the CAS 2 into the sterile confines of the graduated hollow cone 11 without touching any contaminated object. A suitable holder, keeping the open frustum 16 in vertical position when the CAS 2 is being used in a patient, would obviate the utility of such longitudinal flanges 17 and permit alternative use of an over-riding, instead of a reversibly insertable hermetically sealing cap for the trailing open frustum 16 of the graduated hollow cone 11.
(4) Not shown in the figures, the leading end of the barrel on a standard stainless steel CAS is rounded, not abrupt; and the biodegradable plastic material, such as polypropylene, used to construct the graduated hollow cone will stretch some when a rigid cylinder is inserted to the point of wedge impaction IP". Thus, when the leading end of a rigid cylinder, such as a steel CAS or the leading end of a standard disposable syringe is inserted into the cone, the impaction will not be abrupt and the strength of the wedge impaction will be proportional to the force used, especially in a cone whose slope is gradual.
(5) The same principles apply the to the wedge impactions shown at IP'. However, all the elements involved are hollow or solid cones. Cogent here is to note that the open apex 12 of the graduated hollow cone 11 is elongated and almost cylindrical in the leading end, such that maximal surface area is provided for hermetic sealing, as well as directing the inward displacement of the conical needle scabbard 13 such that the contained conical needle hub 15 and needle sharp on each end 14 are displaced accurately in the central axis of the graduated hollow cone 11.

Recommended procedures for use of the graduated hollow cone 11 with a CAS are:
(1) One inloads a sterile-capped carpule 31 into a sterile CAS 2, taking care not to touch the leading piece 1 on the CAS 2 or the penetrable diaphragm 45 in the leading end of the filled carpule 31.
(2) One removes the cap 18 in the open frustum 16 of the graduated hollow cone 11, and inserts the leading end of the CAS 2 to the point of wedge impaction IP" (FIG. 3)
(3) With the CAS wedge impacted, one holds the graduated hollow cone in one hand and grasps the leading end of the conical needle scabbard 13 with the other hand.
(4) One pushes and twists the conical needle, scabbard 13 to break the wedge impaction IP" and advance this scabbard until motion is stopped by contact between the conical needle hub 15 and the leading piece 1 on the CAS 2. Then, one rotates the scabbard clockwise 41 and continues pushing 42 until the inside threads 43 on the conical needle hub 15 mate fully with the outside threads 44 on the leading piece 1 of the CAS. (FIG. 4)
(5) After this mating which extends the trailing end of the needle 14 through the penetrable cap 45 of the filled carpule, one continues clockwise rotation of the conical needle scabbard (so as not to unthread the hub to end piece connection), and pull the empty conical needle scabbard 13 back into its wedge impacted position IP" in the open apex 12 of the graduated hollow cone 11. (FIG. 5)
(6) One then extracts the needle-armed CAS 2 from the graduated hollow cone 11 with the dominant hand holding the trailing end of the CAS and non-dominant hand holding, retracting and twisting the cone to break the wedge impaction IP". After placing the empty graduated hollow cone on a nearby flat surface or in suitable holder, one proceeds to use the armed CAS once or more for the intended purposes, each time returning the CAS back into the cone and into a state of variable wedge impaction immediately after use.
(7) After the final use, the CAS 2 is disarmed by reversing the procedure shown in FIG. 4 through counter-clockwise disengagement of the connection of between the conical needle hub 15 and the CAS end piece 1 and pulling the conical needle scabbard 13 holding the conical needle hub 15 and needle 14 back through the open apex 12 of the graduated hollow cone 11. (FIG. 6).
(8) After removing the disarmed CAS 2 from the graduated hollow cone 11 using both hands, one lays the CAS aside and uses both hands to tighten the wedge impaction IP' of the conical needle scabbard 13 into the open apex 12 in the graduated hollow cone 11, and optionally replace the hermetically sealing cap 18 as a fail safe precaution. Then, the needle sharp on each end 14 inside the graduated hollow cone 11 can be disposed sooner or later together into an appropriate sharps container. (FIG. 7) Alternatively, if an appropriate sharps container with a down-loading entrance is conveniently located, one may eject the conical needle scabbard 13 holding the needle 14 directly into the sharps container and otherwise dispose of the graduated hollow cone 11 and hermetically sealing cap 18.

(9) Subsequently, one may unload the spent carpule 31 into an appropriate container and prepare the empty CAS (FIG. 1) for reuse after proper cleansing and sterilization.

Mutiual Advantages For Dentists and Patients

1. For dentists the graduated hollow cone reduces the chances of accidental needlesticks during the arming and disarming of the CAS and between uses of the needle in patients.
2. For patients the graduated hollow cone minimizes the chances of infection with each injection and reducing the number of injections via the same needle, when more than one dental carpule is needed duiing a given procedure.
3. The increased cost for mutual safety during customary use of standard dental anesthesia needles, CAS and carpules should be minimal, because an inexpensive graduated hollow cone with a hermetically sealing cap merely replaces the trailing cap (not shown) protecting the trailing sharp end of a sterile dental anesthetic needle before use.
4. Moreover, a minimal increase in cost for patients, might well be offset by time saved and efficiency of system during the safe arming and disarming of the CAS by dentists.

B. For Use With a Standard Disposable Luer-Lok Syringe

FIG. 9 shows a similar graduated hollow cone comprising a mid-portion 111, an open apex 112 which reversibly impacts IP' the trailing end of conical needle scabbard 113 holding a hollow bore steel needle 114 sharp on the leading end within a hub 115 which slip connects into the open trailing end of the needle scabbard 113. At the point of wedge impaction IP', the fit between the open apex 112 of the graduated hollow cone 111 and the trailing end of the conical needle scabbard 113 should hermetically seal the open apex 112 of the graduated hollow cone 111. It will be noted that the graduated hollow cone shown here is identical with that shown in FIG. 2, but the dimensions and slopes of the cones differ in order accommodate a standard 3 mL. Luer-Lok medical syringe, abbreviated as LLS. Therefore, the corresponding counterparts are numbered with a 1 prefix.

In the mid-portion of the graduated hollow cone 111, it should be noted that the slope of the puncture-resistant walls are uniform and long, in order to provide maximal surface contact with a cylindrical object inserted to a point of wedge impaction. In the open frustum 116 of the graduated hollow cone, the walls are flared sharply and, then, extended in cylindrical form for four reasons: (a) to maximize the diameter of a target area for insertion of a sharp needle attached to a cylindrical syringe; (b) to provide convenient protrusions for finger placement for users manipulating the graduated hollow cone with one hand; (c) to provide a properly oriented external surface for added longitudinal flutes 117 which will prevent rolling when the graduated hollow cone 111 is placed on a flat or sloped surface; and (d) to provide a cylindrical surface suitable for reversible insertion of a wiling cap 118 for hermetically sealing the graduated hollow cone 111 before use, as well as optional closure after use.

Figure 10:
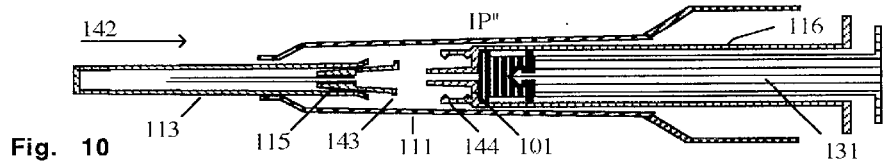
FIG. 10 shows a LLS inserted to a point of wedge impaction in the GHC and the needle-containing scabbard displaced toward the Luer-Lock inside the GHC.

FIG. 10 shows the graduated hollow cone 111 with the leading end of an empty LLS 131 inserted through the open frustum 116 to the point of wedge impaction IP" and the conical needle scabbard 113 pushed 142 from its state of wedge impaction toward the inserted LLS 131. Standard trailing outside flanges 143 on the conical needle hub 115 are depicted clearly. Standard inside threads 144 on the Luer-Lok 101 permanently attached to the LLS 131 are depicted not so clearly.

Figure 11:
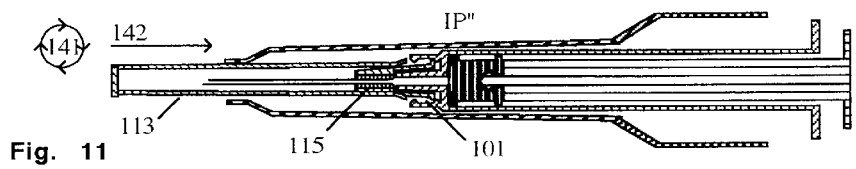
FIG. 11 shows mating of the needle hub to the Luer Lok on the LLS.

FIG. 11 shows the outside flanges on the conical needle hub 115 mated securely with the inside threads in the Luer-Lok 101 by manual clockwise rotation 141 and pushing 142 the conical needle scabbard 113.

Figure 12:
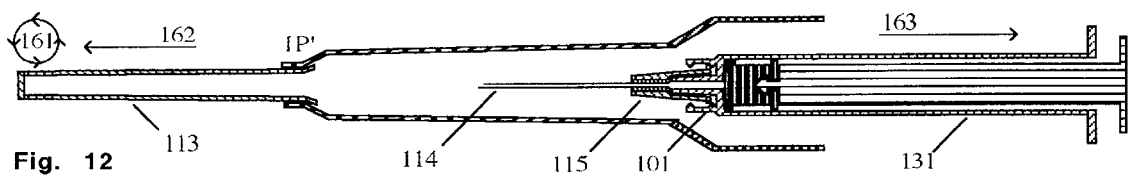
FIG. 12 shows removal of the needle-armed LLS ready for use in a patient.

FIG. 12 shows the conical needle scabbard 113 retracted from the needle hub by manual counter-clockwise rotation 161 and pulling 162 the empty scabbard back into its point of wedge impaction IP'. The sterile hollow bore needle 114 and its hub 115, now firmly attached to the Luer-Lok 101 and trailing LLS 131, is ready for use after retraction 163 of the LLS 131 from its point of wedge impaction.

Figure 13:
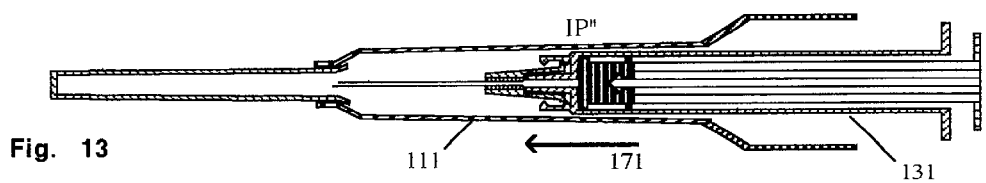
FIG. 13 shows reinsertion of the needle-armed LLS back into the GHC after use.

FIG. 13 does not show interim use for filling the LLS 131 and use in a patient. However, after filling the LLS with a chosen sterile medication, the needle-armed and liquid-filled syringe should be reinserted into the still sterile confines of the graduated hollow cone 111 and wedge impacted IP" therein until just before the injection is given, as depicted in FIG. Immediately after the injection is given, the emptied, but still armed syringe should be reinserted similarly, using extra force 171 to tighten the wedge impaction between the leading end of the IDS and the graduated hollow cone, again as depicted in FIG. 13.

Figure 14:
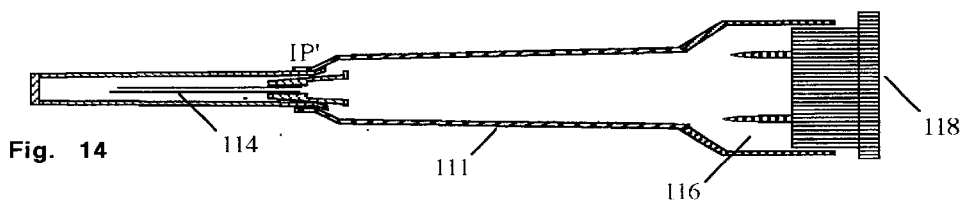
FIG. 14 shows the needle-containing scabbard again safely wedge impacted in the GHC.

FIG. 14 shows the end result, after reversal of relative component positions depicted in FIGS. 10–11, and extraction of needeless LLS 131 shown in FIG. 10. Optional replacement of the hermetically sealing cap 118 into the open frustum 116 of the graduated hollow cone 111 is shown here as a fail safe mechanism, in case of slip-connection or wedge impaction IP' failure.

It should be added that graduated hollow cone 111 provides three options for safe needle disposal:

(1) Disposal of the entire assembly shown in FIG. 13 into an appropriate sharps container.
(2) Separate disposal of the unarmed LLS 131 shown FIG. 10 into hazardous waste and the assembly shown in FIG. 13 into an appropriate sharps container.
(3) Disposal of the disarmed LLS 131 into hazardous waste, disposal of the conical needle scabbard 113 containing the needle hub 115 and the needle 114 into a sharps container by manual downward ejection into a fitting sharps container and disposal of the graduated hollow cone into recyclable waste.

Although the last option might seem to be the most efficient, the options may vary under actual use conditions and experience.

Recommended procedures for actual use of the graduated hollow cone 111 with a LLS 131 are:

(1) One removes the cap 118 in the open frustim of the graduated hollow cone 111 and, then, removes the disposable LLS from a sterile package by grasping the trailing, taking great care not to touch the syringe nozzle inside the Luer-Lok 101, or let the nozzle touch any object.
(2) One inserts the leading end of the LLS 131 through the open frustum 116 of the graduated hollow cone 111 until a point of wedge impaction IP" is reached.(FIG. 10). A little twisting of the LLS while doing so will add tenacity of the wedge impaction.

(3) Then, one grasps the trailing end of the LLS 131 and the mid-portion of the graduated hollow cone 111 with one hand, and uses the other hand to clockwise rotate 141 and advance 142 the conical needle scabbard 115 from its point of wedge impaction toward the Luer-Lok 101 until contact is made between the trailing outside eccentric flanges 143 on the conical needle hub 115 and matching inside threads 144 of the Luer-Lok 101.(FIG. 11) Continued clockwise rotation and advancement will automatically mate the conical needle hub to the Luer-Lok such that syringe nozzle to needle flow without leakage is assured, along with firm attachment of the needle to the syringe.

(4) Then, grasping the graduated hollow cone 111 with one hand and the leading end of the conical needle scabbard 113 with the other, one retracts an empty conical needle scabbard 113 back into its original state of wedge impaction IP' by counter-clockwise rotation and pulling away from the needle firmly attached to the Luer-Lok 101. (FIG. 12).

(5) Then, one may lay aside the graduated hollow cone 111 and contained empty conical needle scabbard conveniently for future use, and extract 163 the needle-armed LLS 131 for intended use in a patient.

(6) Immediately after filling the Luer-Lok syringe 131 from a sterile container, such as a vial or and ampoule (not shown), the filled syringe and Luer-Lok attached needle, one should reinsert the assembly back into the sterile confines of the graduated hollow cone 111 to the point wedge impaction IP" and leave the armed syringe there until actual use of the syringe for injection of the contained medications into a patient (FIG. 13).

(7) Immediately after use of the needle armed LLS 131 in a patient, one should put the leading end of the syringe back into the graduated hollow cone 131 and forcefully 171 create a tenacious wedge impaction of the syringe into the cone (FIG. 13) and, then, disarm the syringe by reversing steps (2–4).

(8) Finally, one may safely dispose of the disarmed empty or partially emptied LLS 131, graduated hollow cone 111 and needle containing conical needle scabbard all together or separately, as previously described. Replacement of the hermetically sealing cap 118 into the open frustum 116 of the graduated hollow cone 111, is not essential because needles used in conjunction with LLS 131 are not sharp on the trailing ends. However, use of the trailing external longitudinal flanges 117 on the flared open frustum 116 of the graduated hollow cone 111, along with the flare for finger placement and large diameter, will make it easy for the user to perform a one-handed recapping of the needle and leading end of the syringe convenient before final disposal, as outlined in (7).

Additional Specifications and Remarks

All the components of dental and medical syringes and needles described and numbered in the foregoing spedifications are traditionally standard in dimensions and usage, except the graduated hollow cone (11,111), the conical needle scabbard (13,113) and the external diameter of Luer-Lok medical syringes (131). "Standard" 3.0 mL LLS 131 are the syringes most commonly used in patients, in conduction with needles ranging from 18–25 Guage in the bore and 0.5 to 1.5 inches in exposed length of the shank. LLS ranging in volume capacity from 1.0 to 30 mL. obviously have differing external diameters in order to conform with traditional or acceptable barrel lengths. The 3.0 mL "standard" LLS produced by Becton-Dickinson, Sherwood and Terumo respectively have syringe barrels measuring ±10.0, 10.08 and 10.1 mm. in external diameter. Although the apically closed conical syringe/shield disclosed in U.S. Pat. No. 5,558,649, after wedge impaction of the leading barrel of each will safely accommodate and shield the shank and needle bevel of each in axial distances successively remote from the apex, the graduated hollow cone 111 described herein will not suit all such disposable syringes, as opposed to the leading ends of CAS 31 whose external diameters more or less constantly measure 10.2 mm. Thus, the graduated hollow cone 11 standard for the CAS is not applicable to 3.0 mL disposable syringes, and the graduated hollow cone applicable to 3.0 mL syringes is not applicable to all without proper modification of the diameeter, slope and length of the conical needle scabbard reversibly held in the open apex (12,112).

In turn, the leading conical needle scabbards for the shank and bevel of standard dental aneesthesia needles sharp on each end and standard syringe-attachable medical needles sharp on the leading end vary widely as produced by different manufacturers. Most are perfectly smooth cones on the inside, made such an inserted needle will not hang up during insertion and made just long enough to accommodate a needle of specified length. On the outside, many are fluted or multiangular, such that the user can manually rotate the scabbard easily to break a seal which covers the junction between leading and trailing scabbards covering needles sharp on each end, or made with distinctive colors to indicate the bore size and length of sterile package-contained needle attatchable to a Luer-Lok syringe. Many, owing to the angle of coning, will wedge impact into an open apex of a graduated hollow cone; owing to flutes or multiangular confifuguration on the outside, but few will hermetically seal the graduated hollow cone at the leading apical end. Thus, in order to fulfill its intended purposes, the hollow conical needle scabbard made for dental and medical needles which inject medications into patients should embody the following additional specifications:

(a) a length sufficient to house the longest needle of selected gauge, plus additional axial length sufficient to manipulate that part of the scabbard with remains exposed when advanced into the graduated hollow cone far enough for the needle hub 15, 115 to be mated with the end piece 1 of a carpule aspirating syringe or the Luer-Lok 101 on any syringe.

(b) a circumferentally smooth surface on the external trailing end of the scabberd which assures hermetic sealing, as well as wedge impaction IP' into the open apex 12, 112 of the graduated hollow cone 11,111.

(c) and, preferably, an external longitinal indicator strip, wide at the frustum and narrow at the apex of the graduated hollow cone for indicating hermetic seal breakage, as well as the contents of the graduated hollow cone.

Disadvantages of such modifications of the hollow needle scabbard are mostly that molds for existing scabbards will need to be modifed, along with labels. Advantages are:

(a) Users will have a wide choice of needle gauges and lengths, all similarly packaged for giving uncontaminated injections into patients and shielding health care workers from accidental needlesticks at relatively low cost compared with other means currently available.

(b) Proportional to use of such hollow needle scabbards for safe keeping of needles in the graduated hollow cones: the reuse of a needle with more than one carpule will be negated in dentristy: the reuse of needles previously attached to Luer-Lok syringe will be negated in medical facilities, and the reuse of syringes/needles will be partly negated apart from healthcare settings, because all the Luer-Lok syringes will lack contaminated needles.

What is claimed is:

1. A needle shield assembly operable for safely handling and containing a hypodermic needle before and alter use thereof comprising:

(d) a needle scabbard comprisrting a tubular body portion having a leading end and a trailing end and a first axial bore therebetween, said first axial bore having a sealed leading end and an open cylindrical trailing end having a bore diameter, said trailing end of said body portion having an expanded conical flange on an outer circumferential surface thereof said flange having a greatest diameter in a direction transverse to said first axial bore, said first axial bore defining a cavity;

(e) a hypodermic needle comprising a shaft having a sharp tip on a leading end thereof disposed within said first cavity and a trailing end having a conical hub affixed thereto wherein a leading portion of said conical hub is disposed within said first cavity, and a trailing portion of said hub is disposed outside of said first cavity, and a wedge portion of said conical hub disposed between said leading and trailing portions of said conical hub, said leading portion of said hub having a diameter less than said bore diameter of said needle scabbard and said trailing portion of said hub has a diameter greater than said bore diameter of said needle scabbard, said wedge portion being reversibly wedged into said trailing end of said first axial bore;

(f) a scabbard container comprising a tubular body portion having a second axial bore coextensive with a length thereof, said second axial bore having an open, cylindrical trailing end having a trailing bore diameter and an open circular leading end having a leading bore diameter wherein said leading bore diameter is less than said trailing bore diameter, and wherein at least a portion or said second axial bore is tapered inwardly toward the leading end thereof; wherein said trailing end of said needle scabbard is disposed within said leading end of said second axial bore and said leading end of said needle scabbard is disposed outside of said second axial bore, and wherein said greatest dimension of said flange is greater than said leading bore diameter of said scabbard container, and wherein said second axial bore is dimensioned to receive a syringe having a leading end adapted to matingly engage said conical hub or a carpule having a puncturable septum.

* * * * *